United States Patent [19]

Umemura et al.

[11] Patent Number: 4,971,991

[45] Date of Patent: Nov. 20, 1990

[54] PHYSIOLOGICAL FUNCTION ENHANCING AGENTS ACTIVATED BY ULTRASONIC WAVES FOR THE TREATMENT OF TUMORS

[75] Inventors: Kohshiro Umemura, Fujisawa; Ryuichiro Nishigaki; Nagahiko Yumita, both of Tokyo, all of Japan

[73] Assignee: Kohshiro Umemura, Kanagawa, Japan

[21] Appl. No.: 274,109

[22] Filed: Nov. 21, 1988

[30] Foreign Application Priority Data

Dec. 1, 1987 [JP] Japan .................................. 62-305317

[51] Int. Cl.$^5$ .............................................. A61K 31/40
[52] U.S. Cl. ..................................... 514/410; 540/145; 204/157.62
[58] Field of Search ........................ 540/145; 514/410; 204/157.62

[56] References Cited

U.S. PATENT DOCUMENTS

| | | | |
|---|---|---|---|
| 4,649,151 | 3/1987 | Dougherty et al. | 514/410 |
| 4,656,186 | 4/1987 | Bommer et al. | 514/410 |
| 4,658,023 | 4/1987 | Shudo | 540/145 |
| 4,675,338 | 6/1987 | Bommer et al. | 514/410 |
| 4,837,221 | 6/1989 | Bonnett et al. | 514/410 |

Primary Examiner—Richard L. Raymond
Attorney, Agent, or Firm—Jordan and Hamburg

[57] ABSTRACT

Physiological function-enhancing agents to be used for the treatment of tumors comprise a compound capable of stimulating the generation of at least one type of active oxygen, such as superoxide radicals and singlet oxygen, upon ultrasonic irradiation (e.g., porphyrins, chlorins, methylene-blue, fluorescein, acridine derivatives, rhodamines and tetracyclines).

Irradiating ultrasonic waves onto tumor tissues, with this agent orally or parenterally administered in advance, causes the active ingredient present at the irradiated site to generate active oxygen (e.g., superoxide radicals and singlet oxygen), which serves to destruct the tumor cells.

These agents are very low in toxicity and exhibit antitumor activity only upon ultrasonic irradiation. Hence, there is no risk of causing any systemic idsorder. In addition, these act exclusively upon tumor tissues when combined with ultrasonic irradiation, with no adverse effect upon normal tissues.

3 Claims, No Drawings

PHYSIOLOGICAL FUNCTION ENHANCING AGENTS ACTIVATED BY ULTRASONIC WAVES FOR THE TREATMENT OF TUMORS

BACKGROUND OF THE INVENTION

1. Field of the Invention

This invention relates to physiological function-enhancing agents to be used for the treatment of tumors, which comprise a compound capable of stimulating the generation of at least one type of active oxygen, such as superoxide radicals and singlet oxygen, by the chemical action caused by irradiation of ultrasonic waves.

2. Description of the Prior Art

As physical methods used for the treatment of solid cancers, radiotherapy (irradiation of X-rays and γ-rays), thermotherapy, laser irradiation and ultrasonic irradiation are known.

Of these, radiotherapy has the disadvantage that sufficient doses to ensure the complete cure of cancers cannot be actually applied because normal tissues are also affected by the irradiation; thermotherapy is no more than an aid to other therapeutical methods; and laser irradiation (a recently developed technique) is poor in the degree of penetration, and hence little effect can be expected except for the treatment of cancers in surface tissues.

Ultrasonic irradiation, on the other hand, is superior to radiotherapy in that the applied waves can be focused solely on the cancer tissues to be treated with little effect upon normal tissues, and is better than laser irradiation in the degree of penetration.

However, application of ultrasonic irradiation for the treatment of cancers has hitherto aimed principally at the destruction of cancer tissues by the physical effects of ultrasonic waves and at the thermotherapeutic effects by its pyretic action, and these effects have been unsatifactory for the complete cure of cancers. As a result, cases are very few in which ultrasonic irradiation was actually applied to the treatment of cancers, despite its better characteristics compared with the other types of physiotherapy.

The present inventors formerly attempted a combination of ultrasonic irradiation with administration of an anthracycline antitumor agent (e.g., adriamycin), and reported the experimental results on their additive or synergistic effects [Japan Hyperthermia, 3 (2), 175–182].

This method proved effective in treating cancers, but is still far from ideal because of the limited dose of antitumor agent as almost all of such drugs have toxicity to a greater or lesser extent.

SUMMARY OF THE INVENTION

Ultrasonic waves are known to show chemical actions; for example, irradiation of water causes a reaction to generate hydrogen peroxide. We extended our studies in search of those compounds which have no antitumor activity and are low in toxicity, and which, when irradiated with ultrasonic waves, undergo a chemical reaction, thereby developing antitumor activity. As a result, it was found that hematoporphyrin, protoporphyrin, pheophorbide, water-soluble chlorophyll derivatives, methylene-blue, fluorescein, acridine-orange, neutral-red and rose-bengal are capable of generating, upon ultrasonic irradiation, active oxygen such as superoxide radicals and singlet oxygen, and the active oxygen thus formed effectively destructs cancer tissues.

This invention was accomplished on the basis of these findings.

Thus, this invention relates to physiological function-enhancing agents to be used for the treatment of tumors which comprise a compound capable of stimulating the generation of at least one type of active oxygen, such as superoxide radicals and singlet oxygen by the chemical action caused by irradiation of ultrasonic waves.

DESCRIPTION OF THE PREFERRED EMBODIMENTS

The active ingredient of the agents of this invention may be any compound which generates at least one type of active oxygen by the chemical reaction caused by ultrasonic irradiation. Preferred examples include porphyrins such as hematoporphyrin and protoporphyrin, chlorins such as pheophorbide, acridine derivatives such as methylene-blue, fluorescein, acridine-orange and neutral-red, rhodamines such as rose-bengal, and tetracyclines.

The physiological function-enhancing agents of this invention may be used in the form of parenteral preparations, such as ointments, liniments, emulsions and injections, or in the form of oral preparations, such as tablets, granules, capsules and solutions. These can be manufactured by the usual techniques using commonly employed base materials.

Cancer treatment by the agent of this invention can be effected by administrating it orally or parenterally and irradiating ultrasonic waves onto the cancer tissues to be treated.

The suitable dose is an amount which is sufficient to enhance the action of ultrasonic waves at the cancer tissues thereby killing the malignant cells. It may vary with the size and position of tumor to be treated, but is generally 1 to 50 mg/kg for intravenous injection and 2 to 100 mg/kg for oral administration when applied to mammals (including humans). The active ingredient of the agents of this invention shows a very low level of toxicity sufficient for practical use—$LD_{50}$ value not lower than 200 mg/kg when intraperitoneally administered to mice.

Irradiating ultrasonic waves onto tumor tissues, with a physiological function-enhancing agent of this invention orally or parenterally administered in advance, causes the active ingredient of the agent present at the irradiated site to generate active oxygen (e.g., superoxide radicals and singlet oxygen), which serves to destruct the tumor cells.

The agents of this invention have no antitumor activity at all, are very low in toxicity, and exhibit antitumor activity only by the chemical action caused by ultrasonic irradiation. Hence, there is no risk of causing any systemic disorder. In addition, these act exclusively upon tumor tissues when combined with ultrasonic irradiation, with no adverse effect upon normal tissues. Furthermore, these can be applied even to tumors developed deeply. Thus the agents of this invention are drugs of high safety with a wide range of application.

This invention will become more apparent from the following examples including test examples showing the tumor cell killing effect of the active ingredient in the agents of this invention.

TEST EXAMPLE 1

(Test on tumor-cell killing effect of hematoporphyrin)

Hematoporphyrin dihydrochloride was used as active-oxygen generator, and sarcoma 180 and AH130 cells were used as tumor cells in this experiment. Sarcoma 180 cells and AH130 cells were injected to the ascites of male ICR mice and to the ascites of male Dawley rats respectively, recovered from the abdomens seven to ten days later, and stored under ice cooling in the form of a suspension in an oxygen-saturated phosphate buffer (PBS, pH 7.4) at a concentration of $4 \times 10^6$ cell/ml.

Ultrasonic waves of 1.92 MHz were generated using a common type of irradiation system at intensities of 1.27, 2.21 and 3.18 $W/cm^2$ and the irradiator was held in a water bath so as to keep the temperature at a constant level during the operation.

To each of the PBS suspensions containing tumor cells, was added hematoporphyrin to final concentrations of 0, 10, 25 and 50 µg/ml, and the mixtures were treated in the irradiator for one minute. At the end of ultrasonic treatment, each mixture was stained with trypan blue, the number of living cells was counted under a microscope, and the cell survival rate was calculated. The result is summarized in Table 1. When hematoporphyrin was added to a concentration of 50 µg/ml and no ultrasonic irradiation was followed, the survival rate was 1.0 for both types of tumor cells.

TABLE 1

| Tumor cells | Ultrasonic intensity ($W/cm^2$) | Drug concn. (µg/ml) | Number of tests | Survival rate |
|---|---|---|---|---|
| Sarcoma 180 | 1.27 | 0 | 3 | 0.843 ± 0.011 |
| | | 50 | 3 | 0.335 ± 0.020* |
| | 2.21 | 0 | 3 | 0.292 ± 0.077 |
| | | 50 | 3 | 0.172 ± 0.058 |
| | 3.18 | 0 | 4 | 0.215 ± 0.051 |
| | | 10 | 4 | 0.140 ± 0.047 |
| | | 25 | 4 | 0.024 ± 0.010* |
| | | 50 | 4 | 0.023 ± 0.002* |
| AH 130 | 1.27 | 0 | 3 | 0.833 ± 0.011 |
| | | 50 | 3 | 0.779 ± 0.016 |
| | 2.21 | 0 | 3 | 0.253 ± 0.018 |
| | | 50 | 3 | 0.054 ± 0.002* |
| | 3.18 | 0 | 3 | 0.142 ± 0.010 |
| | | 10 | 3 | 0.089 ± 0.004* |
| | | 25 | 3 | 0.047 ± 0.006* |
| | | 50 | 3 | 0.045 ± 0.007* |

*Significantly different (P = 0.05) from the case of 0 µg/ml drug concentration (altrasonic irradiation alone)

TEST EXAMPLE 2

(Test on tumor-cell killing effect of hematoporphyrin, protoporphyrin, pehophorbide a, and methylene-blue)

Hematoporphyrin, protoporphyrin, pheophorbide a, and methylene-blue were used as active-oxygen stimulator, and sarcoma 180 and AH130 cells were used as tumor cells (final concentration: 50 µg/ml) in the same manner as in Test Example 1. Ultrasonic waves of 1.0 MHz were irradiated at an intensity of 1.7 $W/cm^2$ and the number of living cells was counted 15, 30 and 60 seconds after irradiation to determine the survival rate.

Table 2 shows the result obtained, in which the data is the average of three tests. When the drug was added to a PBS suspension of tumor cells to a concentration of 50 µg/ml and no ultrasonic irradiation was followed, the survival rate was 1.0 for all the drugs tested.

TABLE 2

| Drug use | Survival rate 15 seconds | 30 seconds | 60 seconds |
|---|---|---|---|
| None | 0.714 ± 0.069 | 0.462 ± 0.055 | 0.269 ± 0.030 |
| Hematoporphyrin | 0.230 ± 0.079** | 0.173 ± 0.048** | 0.050 ± 0.006** |
| Protoporphyrin | 0.145 ± 0.016** | 0.081 ± 0.013** | 0.067 ± 0.013** |
| Pheophorbide a | 0.142 ± 0.031** | 0.079 ± 0.010** | 0.055 ± 0.006** |
| Methylene blue | 0.394 ± 0.056** | 0.238 ± 0.016** | 0.124 ± 0.016** |

**Significantly different (P<0.05) from the case of no drug (ultrasonic irradiation alone)

TEXT EXAMPLE 3

(Test on tumor-cell killing effect of hematoporphyrin)

AH130 cells were transplanted to Dawley rats of 5-week age at the left shoulder to a concentration of $4 \times 10^2$ cell/head, and the tumor developed was allowed to grow to a size of 1 cm or larger (usually taking five days after transplantation).

These rats were divided into four groups, each consisting of four head, and each group was treated as described below.

(1) Control group (group A)

No drug was administered, nor was ultrasonic irradiation performed.

(2) Drug-administered group (group B)

Hematoporphyrin was intravenously injected (50 mg/Kg), but no ultrasonic irradiation was performed.

(3) Ultrasonic-irradiated group (group C)

Ultrasonic irradiation was performed (1 MHz, 1 $W/cm^2$ ×10 minutes), but no drug was administered.

(4) Drug-administered and ultrasonic-irradiated group (group D)

Hematoporphyrin was intravenously injected (50 mg/kg, and ultrasonic irradiation was performed (1 MHz, 1 $W/cm^2$ ×10 minutes) 120 minutes later.

TABLE 3

| Group | Survival time (day) | Number of living rats/Total number tested (after 60 days) |
|---|---|---|
| A | 10.00 ± 0.577 | 0/4 |
| B | 10.25 ± 0.629 | 0/4 |
| C | 10.50 ± 0.645 | 0/4 |
| D | 36.00 ± 13.880 | 2/4 |

As is apparent from the above table, rats of group D showed longer life, 50% of them remaining alive after 60 days.

EXAMPLE 1 (capsules)

Hematoporphyrin: 500 parts

Lactose: 100 parts

Magnesium stearate: 10 parts

The above components were intimately mixed, and the mixture was charged in capsules so that each piece will contain 1000 mg hematoporphyrin.

EXAMPLE 2 (injections)

An aqueous solution of water-soluble chlorophyll was dispensed into vials under germ-free conditions so that each piece will contain 500 mg chlorophyll.

What is claimed is:

1. A method of treating tumors consisting of administering to a host afflicted with cancer tissue, as an active ingredient, a compound capable of stimulating the generation of at least one type of active oxygen through a chemical reaction caused by irradiation of the compound with ultrasonic waves, said compound comprising hematoporphyrin, and a pharmaceutically acceptable carrier therefor, and irradiating said cancer tissue with ultrasonic waves to induce said chemical reaction and stimulate the generation of said active oxygen.

2. A method as in claim 1, wherein said compound is administered intravenously in a dosage of 1 to 50 mg/kg.

3. A method as in claim 1, wherein said compound is administered orally in a dosage of 2 to 100 mg/kg.

* * * * *